United States Patent [19]
Burnouf-Radosevich et al.

[11] Patent Number: 6,069,236
[45] Date of Patent: May 30, 2000

[54] IMMUNOGLOBULIN G CONCENTRATE FOR THERAPEUTIC USE AND PROCESS FOR PRODUCING SAID CONCENTRATE

[75] Inventors: Miryana Burnouf-Radosevich, Aubers; Dominique Dernis, Marquette Lez Lille; Patrick Bonneel, Lille; Thierry Burnouf, Aubers, all of France

[73] Assignee: Association pour l'Essor de la Transfusion Sanguine dans la Region du Nord, Lille, France

[21] Appl. No.: 08/564,030

[22] PCT Filed: Jun. 13, 1994

[86] PCT No.: PCT/FR94/00699

§ 371 Date: Mar. 25, 1996

§ 102(e) Date: Mar. 25, 1996

[87] PCT Pub. No.: WO94/29334

PCT Pub. Date: Dec. 22, 1994

[30] Foreign Application Priority Data

Jun. 14, 1993 [FR] France ................................. 93 07128

[51] Int. Cl.$^7$ ......................................................... C07K 1/16
[52] U.S. Cl. ...................... 530/416; 530/417; 530/387.1; 435/4
[58] Field of Search .................. 530/387.1, 416, 530/417; 435/4

[56] References Cited

U.S. PATENT DOCUMENTS

| | | | |
|---|---|---|---|
| 4,841,024 | 6/1989 | Nathan et al. | 530/387 |
| 4,877,866 | 10/1989 | Rudnick et al. | 530/387 |
| 4,880,913 | 11/1989 | Doleschel et al. | 530/387 |

FOREIGN PATENT DOCUMENTS

| | | |
|---|---|---|
| 0440483 | 8/1991 | European Pat. Off. . |
| 440483 | 8/1991 | European Pat. Off. . |
| 8905157 | 6/1989 | WIPO . |

OTHER PUBLICATIONS

Hooper et al., Central Lab. of the Netherlands Red Cross, *Immunoglobulin Manufacturing Procedures*, pp. 361–380 (1988).

Friesen et al., The Winnipeg Rh Institute Inc., Univ. of Manitoba, *Column Ion Exchange Chromatographic Production of Human Immune Globulins and Albumin*, pp. 118–126 (1982).

Friesen, Joint IABS/CSL Symp. on Standardizatino in Blood Fractionation, Australia 1986, Develop. biol. Standard. 67, 1987, 3–13.

Burnouf T. Bioseparation, 1:383–396, 1991.

Good, RA. et al. Cancer, 68(6 Suppl.) :1415–21, 1991.

*Primary Examiner*—Paula K. Hutzell
*Assistant Examiner*—Minh-Tam Davis
*Attorney, Agent, or Firm*—Birch, Stewart, Kolasch & Birch, LLP

[57] ABSTRACT

The invention relates to a plasma derived immunoglobulin G concentrate and to the process for producing said concentrate. The process comprises a series of chromatographic separations but no ethanol precipitation. The process also includes a viral inactivation treatment. The invention relates to the immunoglobulin G concentrate obtained by said process which is of therapeutic quality suitable for any use especially for intraveinous injection.

9 Claims, No Drawings

IMMUNOGLOBULIN G CONCENTRATE FOR THERAPEUTIC USE AND PROCESS FOR PRODUCING SAID CONCENTRATE

This application is a 371 of PCT/FR94/00699, filed on Jun. 13, 1994.

The invention relates to an immunoglobulin G concentrate suitable for therapeutic use and to the process for producing said concentrate.

Several polyvalent immunoglobulin preparations have been frequently used. In general, they are prepared from a pool of serum from 2000 to 5000 donors which ensures the presence of all the antibodies normally present in the global population of a chosen region.

Those immunoglobulin preparations are produced according to the conventional Cohn method more or less modified, thus by ethanol precipitation. This process has a major disadvantage due to the ethanol treatment which causes some protein denaturation and the formation of immunoglobulin aggregates. These aggregates induce therapeutic adverse reactions due to the activation of the complement system and to anaphylactic reactions. Those preparations are thus unsuitable for intraveinous injections and are only acceptable for intramuscular injection which restricts the amount that can be injected and thus its efficiency.

Several treatments are already performed to solve this problem: pepsin or plasmin cleavage of the immunoglobulins, treatment with β-propiolactone or reducing and alkylating agents, treatment at pH 4, treatment with PEG to cause aggregate precipitation.

The Applicant has preferably avoided those enzymatic or chemical treatments and has deleted the ethanol precipitation step. He has thus set up a process which included serial chromatographic separations and does not include any precipitation step.

An immunoglobulin concentrate has already been prepared by Friesen et al. (Friesen—Joint IABS/CSL Symp. on Standardization in Blood Fractionation—Australia 1986—Develop. biol. Standard. 67, 1987, 3–13; Immunoglobulins—Pub. Central Lab. Netherlands Red Cross 1988—Ed. Krynen, Strengers, Van Aken) using one or two ion exchange chromatographic steps:
- a single chromatography on DEAE-SEPHADEX® is suited for the production of specific γ-globulins from hyperimmune serums but it is only applicable to small amounts.
- a DEAE-SEPHAROSE® chromatography followed by a DEAE-SEPHADEX® chromatography allows processing of larger amounts and is suitable for polyvalent immunoglobulins preparation but it has not be found profitable at an industrial scale.

Immunoglobulin purification involves peculiar problems, in addition to the aforementioned, because their biological activity is linked to their structural integrity, but said activity is not easily measured, as would be the case with an enzymatic activity. As an example, for a given specific antibody, various concentrates showing identical ELISA antibody titres show various degrees of viral infectivity neutralizing capacity, according to their process of preparation.

The Applicant has thus tried to develop a non-denaturing process for immunoglobulin purification, which can be performed on an industrial scale (for example with more than 5000 liters batches of serum) and, moreover, which is compatible with the collection of other proteins of therapeutic value.

The process for producing an immunoglobulin concentrate according to the present invention does not include any ethanol precipitation step and includes a series of chromatographic steps during which the immunoglobulins always remain in liquid phase and at a pH between 5.5 and 7.8. The process also includes a viral inactivation treatment, like solvent-detergent treatment for example.

The process according to the present invention is suited for total plasma or, preferably, for cryosupernatant.

It can be used for large volumes of plasma pools for polyvalent immunoglobulin preparations as well as for smaller volumes of hyperimmune plasmas for specific immunoglobulin preparations.

The plasma or plasma fraction starting material is preferably subjected to a prepurification step, before implementing the claimed process. This prepurification is performed by filtration on a series of cartridges with a porosity of 0.5 to $0.2\mu$, made of cellulose and perlites, negatively charged, and of a small amount of positively charged resin (ZETA PLUS® filters, Cuno, USA). These filters, due to their negative charges, allow Factor IX adsorption which is thus eliminated whereas in the absence of prepurification step it is co-purified with the immunoglobulins, thus possibly inducing adverse reactions and low pressure phenomenon with the final product.

The process possibly comprises one or several prepurification steps allowing to eliminate some plasma proteins and thus to reduce the size of the further chromatographic columns, which is especially worthwhile for large volumes.

The protein fraction can be prepurified batchwise in the presence of an anion exchange gel, like DEAE-SEPHADEX®, which adsorbs and thus eliminates Factor IX, Factor VII and protein C. Afterwards it can be injected onto a column of anion exchange gel, like DEAE-SEPHAROSE®, which adsorbs and thus eliminates albumin and α-antitrypsin. The latter proteins can be desorbed and concentrated according to well-known methods, with an unusually high yield as a side product of the claimed process.

The protein fraction flowing through the previous column can optionally be subjected to a chromatographic step on a heparin-SEPHAROSE® column before the next chromatographic step, in order to eliminate antithrombin III.

The process according to the present invention includes a dessalting step, either by ultrafiltration or by size exclusion chromatography by injecting the filtrate of the optional prepurification steps onto a column of cross-linked dextran type gel, like SEPHADEX® G25, equilibrated with 0.022 M TRIS-HCl buffer, pH 7.8, and harvesting of the plasma proteins containing fraction.

Said proteinaceous fraction is then injected onto an anion exchange chromatographic column, preferably filled with a DEAE-grafted gel. An unusually high yield is obtained with a cross-linked acrylamide type gel like DEAE-TRISACRYL® PLUS LS (SEPRACOR-IBF ref. 262080), equilibrated with 0.025 M TRIS-HCl buffer, pH 7.8. This column adsorbs nearly all the plasma proteins except the immunoglobulins G. They flow through in the filtrate and can be concentrated to 50 g/l.

The concentrated immunoglobulin solution is then subjected to a viral inactivation treatment, for example in the presence of solvent-detergent, preferably like 0.3% TnBP (tri(n-butyl)phosphate) and 1% TWEEN® 80 at 25° C. with light stirring for at least 6 hours.

The process according to the present invention further includes a chromatography on cation exchange gel, preferably with carboxymethyl (CM) groupings grafted gel. An unusually high yield is obtained with a gel like CM-TRISACRYL® LS (SEPRACOR, ref. 260280) equilibrated with 0.024 M acetate buffer, pH 5.5.

This gel adsorbs the immunoglobulins and enables elimination of the solvent-detergent in the filtrate. The immunoglobulins are desorbed and eluted by increasing the ionic strength of the buffer to 0.15–0.19 M NaCl.

110 g/l of saccharose is added to the concentrate which is dispensed and freeze-dried.

Analysis of the immunoglobulin G concentrate obtained by the process as described before indicates that it is devoid of aggregates, of immunoglobulins A and, surprisingly, that is also devoid of immunoglobulins E or that they are only present at a level of 10% of the plasma level, which gives a further therapeutic advantage to the product.

The present invention thus relates to a new plasma derived immunoglobulin G concentrate devoid of aggregated immunoglobulins G, of immunoglobulins E and of immunoglobulins A.

These properties render it especially suitable for intraveinous injection and it is thus conditioned accordingly for said injection.

The following examples provide forms of embodiments of the process according to the invention without, however, limiting its scope.

EXAMPLE 1

The starting material is a 500 liters plasma pool from healthy donors, randomly selected from a normal population.

After cryoprecipitation, according to conventional method, the supernatant is harvested to be subjected to the series of chromatographic steps.

1.A Dessalting Chromatography

This chromatography is performed on a GF 04-06 column (SEPRACOR®) filled with 65 liters of SEPHADEX® G25, equilibrated with 0.022 M TRIS-HCl buffer, pH 7.8, at a flow rate of 450 l/hr.

The filtrate is monitored by densitometry and the fraction containing all the proteins is collected.

The column is regenerated by washing with 1M NaCl solution.

1.B Chromatography on Ion Exchange Gel

This chromatography is performed on a GF 08015 column filled with 65 liters of DEAE-TRISACRYL®, equilibrated with 0.025 M TRIS-HCl, pH 7.8, at a flow rate of 150 l/hr.

Under these implementing conditions, the immunoglobulins G are virtually the only proteins that do not adsorb to the column.

The flow-through filtrate is monitored by densitometry and the protein fraction is collected. It contains immunoglobulins G nearly 100% pure.

Albumin which remains adsorbed on the column can be eluted by adding 0.4 M NaCl into the buffer and it is further concentrated according to conventional methods.

The column is regenerated by washing with 2 M NaCl solution.

1.C Viral Inactivation Treatment

The filtrate of the previous column is concentrated to about 50 g/l and subjected to a known treatment, i.e. by adding a mixture of solvent-detergent for 6 hours at 2520 C. under gentle stirring. The mixture contains 0.3% TnBP and 1% TWEEN 80.

1.D Chromatography on Cation Exchange Gel

This chromatography is performed on a GF 08015 column filled with 65 liters of CM-TRISACRYL® equilibrated with 0.024 M sodium actetate buffer, pH 5.5, at a flow rate of 20 to 100 l/hr.

Under these implementing conditions the immunoglobulins are adsorbed on the gel and the solvent-detergent mixture and possible denatured contaminants or other residues are eliminated in the filtrate.

The immunoglobulins are then desorbed by increasing the ionic strength of the buffer by adding 0.15–0.19 M sodium chloride.

The harvest has an immunoglobulin concentration of 30–50 g/l and can be dispensed without further manipulation after the addition of 110 g/l saccharose.

The column is regenerated by washing with 1M NaCl solution.

EXAMPLE 2

In the process according to example 1, an additional preliminary prepurification step is included, before the first chromatography.

The cryosupernatant is subjected to filtration on a series of 3 cartridges of filters with a porosity of between 0.5 and $0.2\mu$, mainly negatively charged (ZETA PLUS® filters—CUNO—Process filtration products—subsidiary of Commercial Intertech Corp. USA, as described in patents U.S. Pat. Nos. 4,783,262 and 4,859,340, and known as "CUNO filters"). Said filters are made of purified cellulose, perlites and a small amount of positively charged resin. Other commercially available filter systems could also be used.

The filters are rinsed with citrate/phosphate buffer including sodium citrate, disodium phosphate, potassium phosphate, sodium chloride and disodium-EDTA, at a pH of between 5.5 and 6.5, preferably 6.

This filtration step enables adsorption and thus elimination of Factor XI.

EXAMPLE 3

In the process according to example 1 or example 2, an additional preliminary adsorption step is included, performed on anion exchange gel, before the first dessalting chromatography on SEPHADEX® G25.

This preliminary adsorption is performed batchwise in the presence of DEAE-SEPHADEX® 1.5 g per liter of plasma, for 2 to 5 hours. It enables adsorption and thus elimination of Factor IX, Factor VII and protein C. The immunoglobulins are present in the supernatant.

This supernatant can further be subjected to an additional prepurification by column chromatography on DEAE-SEPHAROSE® CL6B FF (Pharmacia-Sweden). The plasma fraction is dialysed and adjusted to 1.6 mS conductivity with 0.025 M sodium acetate, and to pH 7.6. The column is equilibrated with 0.025 M sodium acetate buffer, pH 7.6.

The immunoglobulins flow through into the filtrate.

This process offers 2 advantages:

it lets the prepurified immunoglobulins flow through thus allowing the use of smaller columns for the next steps;

it keeps albumin and α-antitrypsin adsorbed so that they can be collected and purified, according to known methods, with an unasually high yield.

The filtrate, containing the prepurified immunoglobulins G, can be subjected to an additional column chromatography on heparin-SEPHAROSE®. The column is equilibrated with 0.02 M phosphate—0.154 M sodium chloride buffer, pH 6.8.

This chromatography enables the adsorption and thus elimination of antithrombin III while the immunoglobulins flow through into the filtrate.

EXAMPLE 4

The antibody titres and the neutralizing capacity of viral infectivity, for a virus chosen as a model like cytomegalovirus, were compared among immunoglobulins prepared by conventional ethanol fractionation followed by treatment with pepsin at pH 4 and immunoglobulins prepared according to the process of the present invention.

| Process for preparing IgG | ELISA titre (U/ml) | Neutralizing capacity (titre of CMV) |
|---|---|---|
| •conventional method | | |
| batch 1 | | |
| batch 2 | 100 | 1280 |
| batch 3 | 110 | 640 |
| | 110 | 640 |
| •claimed method | | |
| batch 1 | 90 | 2560 |
| batch 2 | 120 | 5120 |
| batch 3 | 100 | 5120 |

The results clearly show that for similar amounts of antibodies (as measured by ELISA), their quality as evaluated by their biological activity (neutralizing capacity) is significantly better for the antibodies produced by chromatographic process.

EXAMPLE 5

The amount of IgE was measured in the starting plasma, in IgG concentrates prepared according to conventional methods (as in example 4) and IgG concentrates prepared according to the chromatographic process of the present invention.

The next table shows that nearly no residual IgE can be found in the chromatographic product whereas IgE are more abundant in conventional preparations than in plasma used as the material.

| | Batch n° | IgE (UI/ml) |
|---|---|---|
| Plasma starting material | 99030120 | 96 |
| | 30162 | 108 |
| | 30170 | 118 |
| Conventional IgG | 50020200 | 293 |
| | 20231 | 259 |
| | 20291 | 272 |
| | 23300 | 220 |
| | 30070 | 230 |
| | 30071 | 210 |
| | 30072 | 246 |
| | 30080 | 242 |
| | 30081 | 258 |
| | 30082 | 248 |
| | 30090 | 214 |
| | 30091 | 212 |
| | 30092 | 170 |
| | 30100 | 160 |
| | 30101 | 117 |
| | 30102 | 144 |
| | 30110 | 250 |
| | 30112 | 224 |
| | 30120 | 195 |
| | 30121 | 161 |
| | 30122 | 220 |
| | 30130 | 238 |
| | 30131 | 248 |
| | 30132 | 227 |

-continued

| | Batch n° | IgE (UI/ml) |
|---|---|---|
| IgG by chromatographic process | 50230050 | 12 |
| | 070 | 6 |
| | 080 | 8, 1 |
| | 090 | 4, 1 |
| | 100 | 7, 5 |
| | 110 | 3, 5 |

We claim:

1. A process for preparing a human polyvalent immunoglobulin G concentrate from plasma, which is suitable for therapeutic use and which does not cause aggregate-induced complement activation and contains a level of immunoglobulin E lower than 10% of the plasma level comprising successively:

(a) a desalting step;

(b) a chromatography on anion exchange gel;

(c) a viral inactivation treatment comprising solvent-detergent treatment;

(d) a chromatography on cation exchange gel; and (e) recovering the immunoglobulin G concentrate.

2. A process according to claim 1, characterized in that an after cryoprecipitation, supernatant plasma fraction from said plasma is used as a starting material.

3. A process according to claim 2, characterized in that the cryoprecipitation supernatant is subjected to a prepurification step by filtration on a series of cartridges of filters with a porosity of 0.5 to 0.2μ, made of cellulose and perlites, negatively charged, and of a small amount of positively charged resin.

4. A process according to claim 2, characterized in that it further comprises one or several prepurification steps by adsorption of some plasma proteins on gels chosen among anion exchange gels and a cross linked agarose which is conjugated to heparin.

5. A process according to claim 1, characterized in that step a is performed on a cross linked dextran gel, equilibrated with 0.022 M TRIS-HCL buffer at pH 7.8, and that the fraction containing the plasma protein is collected to be subjected to step b.

6. A process according to claim 1, characterized in that step b is performed on a cross linked acrylamide gel, grafted with DEAE groupings, equilibrated with 0.025 M TRIS-HCl buffer at pH 7.8, and that the filtrate is collected to be subjected to step c.

7. A process according to claim 1, characterized in that step c is performed by solvent-detergent treatment for at least 6 hours at 25° C.

8. A process according to claim 1, characterized in that step d is performed on a cross-linked acrylamide gel, grafted with carboxymethyl groupings, equilibrated with 0.024 M sodium acetate buffer at pH 5.5, and that the immunoglobulins adsorbed on the gel are eluted by increasing the ionic strength of the buffer to 0.15–0.19 M NaCl.

9. A process according to claim 1, characterized in that the immunoglobulins eluted from step d are supplemented with 110 g/l saccharose and then freeze-dried.

* * * * *